(12) United States Patent
Duval et al.

(10) Patent No.: US 10,612,004 B2
(45) Date of Patent: Apr. 7, 2020

(54) FUNCTIONAL PIGMENTED SKIN EQUIVALENT

(75) Inventors: Christine Duval, Deuil-la-Barle (FR); Françoise Bernerd, Paris (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 12/382,384

(22) Filed: Mar. 16, 2009

(65) Prior Publication Data

US 2009/0239254 A1 Sep. 24, 2009

Related U.S. Application Data

(60) Provisional application No. 61/046,119, filed on Apr. 18, 2008, provisional application No. 61/053,890, filed on May 16, 2008.

(30) Foreign Application Priority Data

Mar. 17, 2008 (FR) ........................ 08 51705
Apr. 29, 2008 (FR) ........................ 08 52886

(51) Int. Cl.
*C12N 5/071* (2010.01)
*G01N 33/50* (2006.01)

(52) U.S. Cl.
CPC ....... *C12N 5/0698* (2013.01); *G01N 33/5088* (2013.01); *C12N 2501/11* (2013.01); *C12N 2501/117* (2013.01); *C12N 2501/39* (2013.01); *C12N 2502/091* (2013.01); *C12N 2502/094* (2013.01); *C12N 2502/1323* (2013.01); *C12N 2533/50* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | | | |
|---|---|---|---|---|
| 5,849,579 | A * | 12/1998 | Li | 435/325 |
| 6,123,959 | A * | 9/2000 | Jones et al. | 424/450 |
| 6,479,072 | B1 * | 11/2002 | Morgan et al. | 424/443 |
| 6,974,697 | B2 * | 12/2005 | Comer et al. | 435/371 |
| 2008/0097607 | A1 | 4/2008 | Bakkar et al. | |

FOREIGN PATENT DOCUMENTS

| | | |
|---|---|---|
| EP | 1 878 790 A1 | 1/2008 |
| FR | 2 879 474 | 6/2006 |
| KR | 10-2007-0055309 | 5/2007 |
| WO | WO 2007/061168 | 5/2007 |

OTHER PUBLICATIONS

Olson A.D. Digestive Diseases and Science. 1993, vol. 38, No. 3, pp. 388-395.*
Tingstrom et al. Journal of Cell Science. 1992, 102, 315-322.*
Duval C. et al. "The use of reconstructed human skin to evaluate UV-induced modifications and sunscreen efficacy" *Experimental Dermatology* vol. 12 No. 2 Jan. 1, 2003 pp. 64-70 XP009051378.
Duval C. et al. "In vitro organotypic models to study skin pigmentation" *Pigment Cell & Melanoma Res.* vol. 21 No. 2 Apr. 1, 2008 pp. 254 XP009106959.
Wang Z. et al. "Effects of aloesin on melanogenesis in pigmented skin equivalents" *Intl. Journal of Cosmetic Science* vol. 30 No. 2 Apr. 2008 pp. 121-130 XP002496633.
Nakazawa K. et al. "Pigmented human skin equivalent: New method of reconstitution by grafting an epithelial sheet onto a non-contractile dermal equivalent" *Pigment Cell Research* vol. 10 No. 6 Dec. 1997 pp. 382-390 XP002480993.
Wang Z. et al. "Effects of aloesin on melanogenesis in pigmented skin equivalents" *Intl. Journal of Cosmetic Science* vol. 30 No. 2 Mar. 13, 2008 pp. 121-130 XP002496633.
Hedley Susan J. et al. "Fibroblasts play a regulatory role in the control of pigmentation in reconstructed human skin from skin types I and II" *Pigment Cell Research* vol. 15 No. 1 Feb. 2002 pp. 49-56 XP002496634.
Archambault M. et al. "Keratinocytes and fibroblasts in a human skin equivalent model enhance melanocyte survival and melanin synthesis after ultraviolet Irradiation" Journal of Investigative Dermatology vol. 104 No. 5, 1995 pp. 859-867 XP009105950.
Nakazawa K. et al. "Pigmented human skin equivalent—as a model of the mechanisms of control of cell-cell and cell-matrix interactions" Medical and Biological Engineering & Co. vol. 36 No. 6 Nov. 1, 1998 pp. 813-820 XP000784856.
Scott G. A. et al. "Keratinocytes Regulate melanocyte number in human fetal and neonatal skin equivalents" *Journal of Investigative Dermatology* vol. 97 No. 5, 1991 pp. 776-781 XP009105906.
Duval et al., CS3-2 *In vitro organotypic models to study skin pigmentation*, The Authors, Journal Compilation (2008) (abstract only).
Duval et al, *The use of reconstructed human skin to evaluate UV-induced modifications and sunscreen efficacy*, 12(Supp 2) Experimental Dermatology 64-70 (2003).
Nakazawa et al., *Pigmented Human Skin Equivalent: New Method of Reconstitution by Grafting an Epithelial Sheet Onto a Non-Contractile Dermal Equivalent*, 10 Pigment Cell Res. 382-390 (1997).

* cited by examiner

*Primary Examiner* — Vera Afremova
(74) *Attorney, Agent, or Firm* — Buchanan Ingersoll & Rooney PC (57) ABSTRACT

An in vitro skin equivalent includes at least one epidermis equivalent and at least one dermis equivalent, and further includes melanocytes constitutively producing melanin and fibroblasts.

14 Claims, 4 Drawing Sheets

Figure 2:

FUNCTIONAL PIGMENTED SKIN EQUIVALENT

CROSS-REFERENCE TO PRIORITY/PCT/PROVISIONAL APPLICATIONS

This application claims priority under 35 U.S.C. § 119 of FR 0851705, filed Mar. 17, 2008, FR 0852886, filed Apr. 29, 2008, and of Provisional Application No. 61/046,119, filed Apr. 18, 2008 and Provisional Application No. 61/053,890, filed May 16, 2008, each hereby expressly incorporated by reference in its entirety and each assigned to the assignee hereof.

BACKGROUND OF THE INVENTION

Technical Field of the Invention

The present invention relates to reconstructed skin having a constitutive pigmentation, and to the use thereof in methods for evaluating skin pigmentation phenomena; it thus relates to methods for evaluating agents capable of modulating this pigmentation, whether it is constitutive or induced. It also relates to a method for preparing such skin models.

Description of Background and/or Related and/or Prior Art

Skin color is principally due to the presence of a pigment, melanin, in the epidermis. Melanin is synthesized by specific dendritic cells located in the basal layer of the epidermis, melanocytes. Melanogenesis takes place in organelles, the melanosomes, which, loaded with melanin, are transferred to the neighboring epidermal cells, the keratinocytes, via the dendrites.

This pigmentation can be modulated by physical factors, such as UV radiation, or chemical factors, such as depigmenting or propigmenting products, and/or during physiological or pathological modifications of the functioning of the skin.

It is therefore desirable to have models which, on the one hand, make it possible to carry out the studies necessary for a better understanding of the role of the skin, both in mechanical terms and in physiological terms, and which, on the other hand, constitute predictive tests for the activity of cosmetic and/or pharmaceutical active agents or else for the side effects of topical ingredients or agents taken orally.

At the current time, in vitro models exist for evaluating a modulation of pigmentation. They are in particular the following models:

inhibition, in tubo, of recombinant human or fungal tyrosinase (solely biochemical, non-cellular model) (*Virador Analytical Biochem.*, 1999);

monolayer monocultures of normal melanocytes or melanocytes derived from melanoma (*Virador Analytical Biochem.*, 1999, Ni-komatsu JID 2007);

monolayer co-culture of normal or immortalized human melanocytes-keratinocytes (*Régnier Cell Mol Biol.*, 1999, Yoon Pigment Cell Res 2003);

pigmented reconstructed epidermis on dead de-epidermalized dermis or on an inert polycarbonate filter: 3D model constituted of melanocytes and keratinocytes only.

For many years, efforts have been made to develop reconstructed skin models which, on the one hand, make it possible to perform the studies necessary for a better understanding of the role of the skin, both in mechanical terms and in physiological terms, and which, on the other hand, constitute predictive tests for the activity of cosmetic and/or pharmaceutical active agents or else for side effects of topical ingredients.

EP 285471 thus describes a method for preparing a skin equivalent from a culture of keratinocytes originating from the sheath of the hair follicle; by seeding on a dermis equivalent, a differentiated epidermis, the structure of which is close to that of the human epidermis, is obtained.

Various skin equivalents have subsequently been proposed, and it has been suggested to introduce melanocytes into these models.

FR 2 689904 and WO 95/10600 describe the preparation of an epidermis equivalent containing keratinocytes and melanocytes, and the use thereof in sun-tanning tests. However, these epidermis equivalents are obtained on an inert support which does not reproduce the physiological interactions with the dermis, and which does not contain fibroblasts or a matrix environment. Furthermore, the culture conditions do not make it possible to keep the melanocytes in a normal phenotype owing to the use of a tumor promoter (TPA or PMA).

However, none of these models makes it possible to provide an understanding of the modulation of pigmentation by the participants of the dermis (fibroblasts, extracellular matrix, dermo-epidermal junction components) since they do not comprise a live dermis.

Even when human organotypic models comprising live fibroblasts are developed, they do not make it possible to evaluate a modulation of pigmentation in a physiological context because they have functionality deficiencies (absence of constitutive pigmentation or pigmentation that can be induced in particular by UV exposure).

Models of pigmented skin have been developed on de-epidermalized dead dermis or on sponge (matrix of collagen+GAGs) recolonized by fibroblasts. However, the localization of the melanocytes therein is often imperfect and these models exhibit functionality deficiencies. Specifically, they show little or no constitutive pigmentation, and the stimulation of pigmentation by UV radiation or by a physiologically propigmenting agent is not observed in these models.

Fibroblasts embedded in a matrix of free collagen (not taut) have also been used to reconstruct a pigmented skin. However, these models have drawbacks which do not enable them to be used to evaluate the modulation of pigmentation.

Bertaux et al. (*Br J Dermatol.*, 1988) developed a model of pigmented skin by introducing a skin biopsy onto the dermal equivalent in order for the epidermal cells to leave the epidermis and proliferate on the surface of the lattice. Among the drawbacks of such a technique, exemplary is the lack of control of the epidermal cells and the fact that only one skin reconstruction is possible with a biopsy: no experiment is therefore comparable to the other (no reproducibility). Furthermore, like the model developed by Haake and Scott (Scott and Haake, *J. Invest Dermatol.*, 1991), this model does not show any real functionality: neither the constitutive nor the induced presence of melanin is observed.

In the model by Archambault et al. (*J Invest Dermatol.*, 1995), melanogenesis stimulation is induced after UV-B radiation, but for doses that induce epidermal alteration (cytotoxic dose) constituting conditions that are completely unacceptable for being able to study pigmentation and the modulation thereof in an in vitro context close to the physiological context.

Other more recent attempts at reconstructing a pigmented reconstructed skin have been made on a free lattice support;

however, the models obtained do not correspond to models of normal human skin because, either they are created using mouse melanocytes (Yoshimura J *Dermatol Sci.*, 2001), or the melanocytes are cultured under conditions which induce tumor transformation, in the presence of TPA (Liu *Cell Biol Int.*, 2007). As for the model developed by Martinhao Sauto et al. (*Sao Paulo Med J.*, 2006), no melanocyte is present or it is not shown in the epidermis.

Need therefore exists for a model making it possible to obtain a relevant understanding of the skin and the disruption thereof, reproducing the physiological interactions of human skin.

Need also exists for methods for evaluating the modulation of skin pigmentation, which make it possible to gain a relevant understanding of all the mechanisms involved in skin pigmentation and the disruption thereof, reproducing the physiological interactions of human skin.

In particular, need exists for a skin equivalent comprising functional live melanocytes having a similar localization to that which exists in human skin and a dermal compartment with live fibroblasts.

SUMMARY OF THE INVENTION

The present invention thus features an in vitro skin equivalent, which comprises at least one epidermis equivalent and at least one dermis equivalent, and which further comprises melanocytes which constitutively synthesize melanin; this melanin is transferred to the keratinocytes. The skin equivalent according to the invention also contains live fibroblasts.

The skin equivalent according to the invention therefore exhibits a constitutive pigmentation, i.e., pigmentation in the absence of any stimulation by UV radiation or by propigmenting active agents. The term "constitutive pigmentation" means the ability of the melanocytes to produce melanin in the un-stimulated basal state. This pigmentation corresponds to the existence of melanocytes which, under physiological conditions, produce a mature melanin inside melanosomes; the melanin is transferred, by means of the dendrites of the melanocyte, to the keratinocytes, which provide a homogeneous distribution of the pigmentation in the epidermis equivalent. The presence of melanin granules in the melanocytes and the neighboring keratinocytes attests to the constitutive pigmentation The invention more particularly relates to a human skin equivalent.

In particular, the invention features an overall and functional pigmentation unit (or complex) including normal human melanocytes, keratinocytes and fibroblasts and a matrix environment; said unit (or complex) comprises at least one epidermis equivalent and at least one dermis equivalent, and comprises a constitutive and functional pigmentary component (pigmentation which is constitutive and inducible under physiological conditions).

The present invention also features a method for evaluating the ability of an agent to modulate pigmentation, wherein:

(a) said agent is applied to an in vitro skin equivalent, said skin equivalent comprising at least one epidermis equivalent comprising malanocytes constitutively producing melanin, and at least one dermis equivalent comprising live fibroblasts, and (b) the pigmentation (i) of the in vitro skin equivalent to which the agent to be evaluated has been applied is compared with that (ii) of a control skin equivalent which has not been subjected to the agent.

The term "an" agent should be understood to mean, throughout the present description, "at least one", unless otherwise specified.

DETAILED DESCRIPTION OF BEST MODE AND SPECIFIC/PREFERRED EMBODIMENTS OF THE INVENTION

The modulation of the pigmentation in the broad sense can be assessed qualitatively and quantitatively, for the purposes of comparison. Use may be made of any methods for analyzing:

the pigmentation and/or the color of the skin equivalent and the amount and nature of the melanin, and its transfer into and degradation in the keratinocytes; by way of example, exemplary are methods by direct or indirect spectrocolorimetry (measurement of luminance and ITA), by selective spectroscopy (mexameter measurement), by siascopy, by high performance liquid chromatography HPLC measurement (measurement of DHI-melanin, DHICA melanin, pheomelanin) by visible spectrophotometry after dissolving the skin with soluene or sodium hydroxide, by image analysis after staining the melanin with Fontana-Masson, by confocal and multiphoton imaging, by electron paramagnetic resonance, by transmission electron microscopy;

the number, shape and maturity of the melanosomes produced in the melanocytes, transferred into and/or degraded in the keratinocytes;

the amount, maturity and/or enzyme activity of the proteins of the melanosome, such as, for example, pmel-17, tyrosinase, TRP-1, TRP-2 (DCT), MATP, protein P MART-1, SCL117A, SLC24A5 (nckx5), OA1;

the number, distribution, morphology (dendricity) of the melanocytes;

the amount, maturity and/or enzyme activity of the receptors, molecules, transcription factors, at the membrane, cytosolic and nuclear level, which participate in the pathways of melanogenesis, of transport in the dendrites and of transfer of the melanins and of the melanosomes into the keratinocytes. Examples are MC1-R, m-KIT, ETB-R, ETA-R, MITF, USF-1, SOX10, myosin Va, Rho, Rac, Rab27A, melanophilin.

The methods employed may be methods for evaluating the amount and the activity of the proteins and of the expression of the coding gene thereof, such as Dopa-reaction, immunohistochemistry, histological staining, image analysis, molecular biology (PCR), biochemistry (WB, ELISA enzymatic immunoassay), etc., techniques.

The method employs more particularly a human skin equivalent, and in particular a skin equivalent comprising at least melanocytes and/or keratinocytes and/or fibroblasts derived from human skin, advantageously comprising at least melanocytes from human skin.

In particular, the method thus applies to an overall and functional pigmentation unit (or complex) including normal human melanocytes, keratinocytes and fibroblasts and a matrix environment; said unit comprises at least one epidermis equivalent and at least one dermis equivalent, and comprises a constitutive and functional pigmentary component (pigmentation which is constitutive and inducible under physiological conditions).

In fact, it has been found within the context of the invention that it is possible to provide a model which meets the needs summarized above, and which has the following characteristics:

It contains the major cell participants involved in pigmentation, i.e., the melanocyte, but also the main cell partners thereof: keratinocytes and fibroblasts.

It reproduces the three-dimensional organization of the skin in order to respect and enable the contacts and the influences that naturally exist from cell partners, the dermo-epidermal junction and the extracellular matrix.

It is functional, i.e., pigmented in the basal state (constitutive pigmentation) and capable of being stimulated by UV radiation and/or by propigmenting agents, under conditions which reproduce physiological phenomena.

The model according to the invention contains the three major cell types present in the skin and involved in pigmentation, in an architecture close to that of the skin, and thus makes it possible to reproduce the regulation of the melanocyte and of pigmentation by its cell partners and the extracellular matrix.

Indeed, in the skin, the pigmentary cells are closely linked to the neighboring epidermal and dermal cells. By virtue of the localization thereof in the basal layer, at the epidermal-dermal interface, physical and chemical links exist from melanocytes and keratinocytes and also from melanocytes and fibroblasts. A function of these interactions with these two cell types is regulation of the melanocyte and of pigmentation.

It is recognized that, by means of paracrine factors released by keratinocytes and by the direct physical connections established by E-cadherins, the keratinocytes regulate adhesion, growth and survival of melanocytes, and the amount and quality of melanin produced. Among these factors, exemplary are alpha melanocyte stimulating hormone (MSH), endothelin 1 (ET1), stem cell factor (SCF), prostaglandins E2 and F2α (PGE2, PGF2α), basic fibroblast growth factor (bFGF) or nerve growth factor (NGF).

Similarly, the role played by fibroblasts in pigmentation is now indisputable: by secreting factors identical to those produced by keratinocytes, such as bFGF, SCF or hepatocyte growth factor (HGF) or factors which are different, such as dickkopf1 and matrix proteins, fibroblasts modulate the development, growth, morphology and differentiation of melanocytes.

Moreover, the components of the dermo-epidermal junction, the molecules of the dermal extracellular matrix (ECM) also have an impact on the melanocyte and the pigmentation. This is because the melanocytes adhere to the molecules of the basal membrane, via integrins and receptors, in particular to laminin and to collagen IV, and the presence of the molecules of the basal membrane is necessary for the correct basal position of the melanocytes. The quality of the dermo-epidermal junction (or DEJ), which the components and their localization result from the interaction from fibroblasts and keratinocytes, influences the type of anchoring (integrins) at the DEJ.

Modulation of the ECM proteins derived from fibroblasts also affects the proliferation, morphology and melanogenic activity of normal melanocytes. In particular, collagen I, collagen IV, fibronectin and laminin stimulate tyrosinase activity, and modulate the dendricity of melanocytes and the proliferation thereof.

Furthermore, regulatory cell loops exist: keratinocytes can act directly on melanocytes or indirectly on fibroblasts which in turn will modulate melanocytes: for example, the secretion of IL-1α and TNF-α by keratinocytes can stimulate the production of HGF and of SCF by fibroblasts, which in turn activate melanocytes. Similarly, fibroblasts may release cytokines which stimulate keratinocytes (KGF for example). These keratinocytes will in turn produce pigmentation modulation factors.

It is also known that exposure of the skin to sunlight induces a stimulation of pigmentation; this is tanning, which corresponds to a transient activation of melanocytes and an increase in melanin synthesis.

This response is largely due to the contribution of the paracrine factors of the partner cells, keratinocytes and fibroblasts, the production of said paracrine factors being increased by the UV radiation.

The model according to the invention unexpectedly makes it possible to reproduce these phenomena and therefore to test substances or stimuli capable of modifying skin pigmentation.

The method of evaluation according to the invention makes it possible to take into account all these phenomena and therefore to evaluate the ability of substances or of stimuli capable of modulating skin pigmentation, directly and/or indirectly.

The skin equivalent—or reconstructed skin—according to the invention has a stratified differentiated epidermis equivalent comprising at least one superficial layer and at least one basal layer. Advantageously, the keratinocytes reproduce the characteristics of an epidermis in vivo, i.e., a stratified multilayer epithelium with a basal layer in contact with the dermis equivalent and the upper strata of which reflect a differentiation, reproducing, from deep down to the periphery, a suprabasal layer (or prickle cell layer), a granular layer (stratum granulosum) and a horny layer (stratum corneum) of an epidermis. A superficial layer of the epidermis equivalent is to be understood as meaning at least one layer corresponding to a superbasal, granular or horny layer.

The keratinocytes included in the epidermis equivalent can be prepared according to any known method of the prior art. One example is culturing from dissociated epidermis originating from a normal or pathological skin sample.

Preferably, according to the invention, the keratinocytes used are prepared from dissociated epidermis originating from a normal or pathological human skin sample, in particular according to the method described in Rheinwald and Green, *Cell*, vol. 6, 331-344, 1975. They may originate from Caucasian, Asian or African skin, from various anatomical sites (such as, in particular, back, face, breast, back of the hands, palms, etc.), from areas which have or have not been exposed to sunlight. Keratinocytes originating from normal skin may be used. According to one particular embodiment of the invention, use may also be made of keratinocytes originating from skin pathologies such as, for example, age spots (actinic lentigo), melasma, vitiligo, nevus, xeroderma pigmentosum or melanoma. They may also be genetically modified keratinocytes overexpressing or underexpressing certain genes.

The melanocytes are integrated into the epidermis and are localized in the basal layer of the epidermis equivalent according to the invention. These melanocytes are distributed homogeneously in the epidermis equivalent, i.e., their distribution density is substantially constant in a plane parallel to the surface of said dermis equivalent and substantially similar to that found in human skin. All of the melanocytes are thus in the basal layer of the epidermis equivalent according to the invention, the absence of melanocytes in the suprabasal layers and the stratum corneum of the epidermis equivalent attesting to the quality of the reconstruction.

The melanocytes are melanocytes originally from adult, young or newborn human skin, in particular adult human skin. Such melanocytes express the TRP-2 enzyme, unlike melanocytes of the hair follicle. The nature of the melanin synthesized is therefore different: the melanocytes in the epidermis produce eumelanin composed of DHI-melanin and of DHICA-melanin, whereas the melanocytes in the hair produce principally DHI-melanin only, due to the absence of TRP-2 expression.

Moreover, the principal physiological stimulus of skin melanocytes is UV radiation, which, by activating melanogenesis and redistribution of melanin, induces browning of the skin, tanning. This physiological functionality does not involve hair melanocytes, the pigmentation of which is not induced by UV radiation.

The melanocytes may originate from Caucasian, Asian or African skin, from various anatomical sites (such as, in particular, back, face, breast, back of the hands, palms, etc.), from areas which have or have not been exposed to sunlight. Melanocytes originating from normal skin may be used. According to one particular embodiment of the invention, use may also be made of melanocytes originating from skin pathologies such as, for example, age spots (actinic lentigo), melasma, vitiligo, nevus, xeroderma pigmentosum or melanoma. They may also be genetically modified melanocytes overexpressing or underexpressing certain genes.

The melanocytes localized in the basal layer produce melanosomes and melanin which are transferred into the neighboring keratinocytes. The phenotype of skin having a more or less intense constitutive pigmentation linked to the type of melanocytes can thus be reproduced. The constitutive pigmentation can be quantified by any method for measuring pigmentation or the amount of melanin, for example, by spectrocolorimetry (measurement of luminance), by high performance liquid chromatography HPLC measurement, by visible spectrophotometry after dissolution of the skin with soluene or sodium hydroxide, or by image analysis after staining of melanin with Fontana-Masson, by confocal imaging or multiphoton imaging.

Advantageously, the skin equivalent according to the invention has a luminance, measured according to the technique of Chardon et al. (In Biological responses to ultraviolet A radiation, *Ed Urbach* 1992), of less than or equal to 80, in the absence of any exposure to UV radiation and/or to a propigmenting agent. This value may be lower, in particular in the case of an African skin equivalent, and may in particular range from +80 to −40 for phenotypes ranging from very light to black. In general, the pigmented reconstructed skin according to the invention has a difference in luminance (Delta L) of at least 1.5 compared with a reconstructed skin comprising no melanocytes, in the absence of any UV irradiation.

The dermis equivalent according to the invention comprises fibroblasts of which the principal axes are oriented in at least two perpendicular directions. Advantageously, the percentage of fibroblasts oriented longitudinally relative to the surface of the dermis equivalent is less than 50%.

The dermis equivalent comprises a free collagen matrix or lattice, which is contractile in all directions, and homogeneous, without biopsy; the fibroblasts, and where appropriate other cells of the dermis, are distributed in a continuous collagen gel.

The dermis equivalent comprises at least one matrix of collagen type I in which the fibroblasts are distributed. It may also contain other extracellular matrix constituents. The term "extracellular matrix constituent" is in particular molecules such as collagens, in particular collagen IV, laminins, entactin, fibronectin, proteoglycans, glycosaminoglycans or hyaluronic acid. According to one of the embodiments of the invention, the dermis equivalent contains at least collagen IV and laminin; preferably, it also contains entactin. The concentrations of these various constituents may be adjusted by those skilled in the art and will be, for example, for laminin, from 1% to 15% of the final volume, for collagen IV, from 0.3% to 4.5% of the final volume and for entactin, from 0.05% to 1% of the final volume.

The collagen used may be collagen of bovine origin, from rat tail or from fish, or any other source of natural collagen or collagen produced by genetic engineering which allows contraction in the presence of fibroblasts.

The matrix is a gel of collagen which is not taut, obtained by contraction both horizontally and vertically, which does not impose a preferential organization of the fibroblasts. Such a matrix, also termed "free", does not adhere to the support and the volumes thereof can be modified without limit, conferring on it a varying thickness and diameter; the thickness of the dermis equivalent would generally be at least 0.05 cm and in particular approximately from 0.05 to 2 cm, but may be increased without harming the advantageous properties of the skin equivalent according to the invention; similarly, its thickness will be adjusted by those skilled in the art from approximately 3 mm to 20 cm or more.

From the dermal compartment comprising the live fibroblasts and the multistratified epidermis equivalent, contact is direct and constitutes a dermo-epidermal junction similar to that which exists in vivo, both from a structural point of view and from a biochemical point of view. From the biochemical point of view, it comprises components of the basal membrane; of the lamina densa, of the lamina lucida and of the sub-basal zone, such as, inter alia, collagen IV, collagen VII, laminin 5, entactin or fibronectin.

The skin equivalent, which is of use in the method of evaluation according to the invention, can also contain endothelial cells, dermal papilla cells, immune system cells, such as lymphocytes, dendritic cells, macrophages or Langerhans cells, adipocytes, nerve cells, and mixtures thereof.

As indicated above, the skin equivalent exhibits constitutive pigmentation, and the pigmentation may also be increased by exposure to a propigmenting agent and/or to UV radiation.

In particular, after stimulation with UV radiation at doses equivalent to the daily or zenithal irradiation received by a human skin of an individual under physiological conditions, the fibroblasts of the model according to the invention produce cytosoluble factors such as cytokines or growth factors which participate in pigmentation and/or in the modulation thereof.

Furthermore, the number of melanocytes in the basal layer increases after stimulation by UV radiation, in particular by a factor of at least 1.5, and the morphology of said melanocytes is modified: they show a marked increase in dendricity through an increase in the number of dendrites and also the extension thereof; the amount of melanin is also increased by synthesis and by increasing the transfer into the epidermal layers by a factor of greater than or equal to 1.5.

The increase in pigmentation is evaluated by measuring the variation in luminance of the skin or any other methods for quantifying melanin, for instance by measurement using high performance liquid chromatography HPLC, by visible spectrophotometry after dissolution of the skin with soluene or sodium hydroxide, by image analysis after staining of the melanin with Fontana-Masson, or by confocal or multiphoton imaging.

The physiological functionality of the model according to the invention after UV radiation is therefore shown by the changes in the following parameters:

Macroscopic color: the skin exposed to UV radiation is much darker than the non-exposed skin: this macroscopic stimulation of pigmentation is quantified by the decrease in luminance (DL=4.38).

The melanocyte density: the melanocyte density after UV radiation is increased as in normal skin.

The amount of melanin: the pigmentation is really stimulated after UV radiation: the amount of melanin is increased and this increase is quantified by image analysis, after Fontana-Masson staining (staining to reveal the melanin granules) or by assaying after extraction with soluene or sodium hydroxide.

This invention also features a method for preparing such a skin equivalent. The method comprises in particular the following steps:

a) bringing fibroblasts and a solution of collagen into contact, then incubating for a sufficient period of time to obtain a contracted collagen matrix in which the fibroblasts are distributed, constituting a dermis equivalent, b) seeding, with a mixture of keratinocytes and melanocytes, the dermis equivalent obtained in a), and immersion culture in a liquid medium, c) immersion of the entire culture (keratinocytes and melanocytes seeded on the dermis equivalent) obtained in b), and continuation of the culture at the air-liquid interface until a pluristratified epidermis equivalent containing melanocytes, on a dermis equivalent containing fibroblasts in a collagen matrix, constituting a skin equivalent, is obtained.

Preferably, the epidermis equivalent forms horny layers and the melanocytes are located on the basal stratum.

The skin equivalent thus obtained can be removed or used on its support in various methods of evaluation.

Step a) can be carried out with collagen type I, in particular of bovine origin, or a mixture of collagens I and III (approximately 30% relative to the final volume of the lattice) in homogeneous suspension. Advantageously, other constituents are added thereto, such as laminin (in particular, from 1% to 15% relative to the final volume), collagen IV (in particular, from 0.3% to 4.5% relative to the final volume) and/or entactin (in particular, from 0.05% to 1% relative to the final volume) so as to obtain a homogeneous suspension.

The fibroblasts are obtained from human skin, advantageously from adult skin. They may be papillar and/or reticular fibroblasts, alone or as a mixture in any proportion, derived from Caucasian, Asian or African skin, from various anatomical sites (back, face, breast, back of the hands, palms, etc.), from areas which have or have not been exposed to sunlight. In one particular embodiment, use is made of fibroblasts originating from skin pathologies such as, for example, age spots (actinic lentigo), melasma, vitiligo, nevus, melanoma or xeroderma pigmentosum. They may also be genetically modified fibroblasts overexpressing or underexpressing certain genes.

They are cultured in a suitable medium, known to those skilled in the art, and then suspended before mixing with the suspension of collagen and growth factors. The mixture is incubated for 1 to 6 days, preferably for 4 or 5 days, at a temperature of approximately 37° C., generally from 36° C. to 37.5° C. Advantageously, the mixture is incubated on a support which does not allow adhesion thereof, in particular which prevents adhesion of the mixture to the edges of the support; such a support may in particular be obtained by prior treatment of its surface, for example by coating said surface with bovine albumin or serum. A collagen gel which is contracted freely in several directions, while discharging the nutritive medium, and in which the fibroblasts are embedded, is thus obtained.

In order to carry out step b), use is made of keratinocytes originating from human skin, preferably from adult human skin. They may originate from Caucasian, Asian or African skin, from various anatomical sites (back, face, breast, back of the hands, palms, etc.), from areas which have or have not been exposed to sunlight. In one particular embodiment, use is made of keratinocytes originating from skin pathologies such as, for example, age spots (actinic lentigo), melasma, vitiligo, nevus or melanoma. They may also be genetically modified keratinocytes overexpressing or underexpressing certain genes.

A preparation of keratinocytes can be obtained according to conventional cell culture methods.

In particular, the following procedure may be carried out, using a skin explant taken from an individual:

the subcutaneous tissue is removed using a scalpel;

the skin sample is decontaminated by antibiotic treatment (for example: gentamycin):

the dermis is separated from the epidermis by proteolytic treatment (for example: trypsin and dispase) and then dissection;

the dissociation of the cells is subsequently promoted in the presence of a solution of 0.05% trypsin and 0.02% EDTA; the effect of the trypsin is neutralized by adding a DMEM culture medium containing 10% of serum;

the cell suspension is homogenized and subsequently washed in keratinocyte culture medium according to the technique of Rheinwald and Green (*Cell*, 1975).

The keratinocytes are amplified before seeding according to the technique of Rheinwald and Green (*Cell*, vol. 6, 331-344, 1975) by culture on a feeder support constituted of 3T3 fibroblasts in a suitable medium known to those skilled in the art, in the presence of growth factors, in particular of amino acids, serum, cholera toxin, insulin, triiodothyronine and pH buffer solution. In particular, such a culture medium may especially contain at least one mitogenic growth factor for keratinocytes (for example, epidermal growth factor (EGF) and/or keratinocyte growth factor (KGF), in particular KGF), insulin, hydrocortisone and, optionally, an antibiotic (for example: gentamycin, amphotericin B).

Advantageously, said medium may also comprise serum or a pituitary extract, for example of bovine origin, epinephrin, transferrin and/or nonessential amino acids.

The melanocytes are melanocytes originating from young or adult human skin, derived from Caucasian, Asian or African skin, from various anatomical sites (back, face, breast, foreskin, back of the hands, palms, etc.), from areas which have or have not been exposed to sunlight. In one particular embodiment, use is made of melanocytes originating from skin pathologies such as, for example, age spots (actinic lentigo), melasma, vitiligo, nevus or melanoma. They may also be genetically modified melanocytes overexpressing or underexpressing certain genes.

They are amplified by culture in a suitable medium, in the absence of phorbol ester, composed of a base medium such as DMEM/F12 or MCDB153 and supplemented with melanocyte-specific growth factors (such as, for example, bFGF, SCF, ET-1, ET3 or αMSH), and in particular in M2 medium (Promocell) or in other media such as M254 (Cascades Biologics™).

Cell suspensions of melanocytes and of keratinocytes are prepared from these cultures, and mixed so as to obtain mixed keratinocyte/melanocyte suspensions. The melanocyte/keratinocyte ratio may be from 1:10 to 2:1, and is generally approximately 1:1.

The method for preparing a skin equivalent according to the invention therefore comprises steps during which the keratinocytes and the melanocytes are amplified separately in their own growth medium. The cells are then detached and directly co-seeded onto the dermal equivalent at a defined density and a defined ratio.

This method involves greater flexibility and the possible control of each of the cell types during the amplification and during the seeding of the epidermal cells onto the dermis equivalent. This control of the amount of each of the cell types seeded and also of the ratios is an advantage for industrial application in terms of control of the epidermal reconstruction and of reproducibility.

It can therefore be seen that, according to embodiments of the invention, use may be made of keratinocytes and melanocytes from normal skin, or else use may be made of melanocytes and keratinocytes originating from skin pathologies, or even use may be made of one of the 2 cell types originating from skin pathologies and the other corresponding to normal, healthy cells.

This mixed suspension is deposited on the dermis equivalent; the dermis equivalent is advantageously attached to a support via a biological material such as collagen. The melanocyte/keratinocyte suspension is deposited in a ring or any equivalent means for maintaining it on a delimited surface part. A liquid nutritive medium is added in such a way as to cover the mixture of cells; this medium contains growth factors known to those skilled in the art, in particular EGF and/or KGF. The medium will be replaced regularly and the culture continued as an immersion, generally for a period of from 2 to 10 days, in particular from 5 to 8 days, and approximately 7 days. The medium will advantageously contain KGF starting from the 2nd day of immersion, and ideally starting from the 4th day of immersion.

As indicated above, the dermis equivalent may comprise normal fibroblasts and/or fibroblasts of pathological origin. These various types of dermis may be combined with an epidermis equivalent prepared from normal or pathological keratinocyte/melanocyte mixtures, according to the various embodiments described above.

The skins are subsequently, in a manner known per se, immersed so as to obtain differentiation of the keratinocytes and formation of a stratified epidermis equivalent. This step c) corresponding to the culture as an immersion at the air-liquid interface is continued until a differentiated structure is obtained, in general approximately 7 days. However, step c) may be continued for a longer period of time, for example for approximately 28 days, while at the same time conserving a skin equivalent having the advantageous characteristics specified in the above text. The nutritive culture medium will be refreshed regularly. The skin equivalent is subsequently removed so as to perform required tests.

The method of preparation does not employ a mutagenic substance such as TPA or PMA, and the cells do not exhibit any modifications of tumor type.

The skin model that can be obtained according to the invention exhibits constitutive pigmentation, and a functionality allowing inducible pigmentation, this being the case for an in vitro model, without any grafting onto a more complete living organism.

The skin model according to the invention makes it possible to understand the pathway for regulating melanogenesis from every angle. This may be reflected by a direct activity on the melanocyte, but also by a (propigmenting or anti-pigmenting) activity mediated by the keratinocyte, the fibroblast, the entire three-dimensional context and the influence of the microenvironment.

It is useful in particular in various methods of evaluation.

The agent to be evaluated in the implementation of the methods according to the invention may be any chemical or biological substance or compound, or any physical treatment or phenomenon, that may modulate or that is capable of modulating pigmentation, directly or indirectly.

By way of example of a physical treatment that can be evaluated according to the invention, mention may be made of light radiation, for example UV or IR radiation, in particular with an LED (light emitting diode) treatment.

The expression "application of the agent to the skin equivalent" means the fact of provoking an interaction from the agent to be evaluated and at least one part of the skin equivalent, whether by direct contact or by any other means.

The invention features in particular a method of screening for an agent that may modulate pigmentation, it being possible for said agent to be a compound or a mixture of compounds, obtained in particular by chemical synthesis or by extraction from starting material of plant or bacterial/yeast origin. The method will be of particular value for screening for and identifying active agents that are of use in the cosmetics field. The agents may thus be any molecules, growth factors, retinoic derivatives, hormone or plant extracts that can affect the epidermal, dermal or junctional compartment. The modulators may be siRNAs or antagomirs.

The method may also be of value for evaluating the pigmentation modulation of active agents that are useful in the pharmaceutical field, in particular in dermatology.

According to another embodiment, the method according to the invention will make it possible to evaluate the modifications of the various factors involved when a pigmentation-modulating agent is applied.

The term "modulating pigmentation" means, according to the invention, modifying the level of constitutive or induced pigmentation of the skin, either by increasing it, or by decreasing it or by inhibiting it, whether directly or indirectly.

In the method according to the invention, the control skin equivalent will be prepared and stored under conditions identical to those of the skin equivalent to which the agent to be evaluated is applied, and the measurement of the pigmentation will be carried out at identical times on the control skin equivalents and that having received the agent to be evaluated.

According to one embodiment, the agent to be evaluated is applied by direct contact with at least one part of the skin equivalent. According to another embodiment, the agent may also be applied in the culture medium of said skin equivalent, or even with a means that will bring about an indirect interaction of the agent with one of the constituents of the skin equivalent. By way of a non-limiting alternative method of applying the agent to the skin equivalent, mention may in particular be made of injection, mesotherapy or iontophoresis.

The agent to be evaluated can, in particular, be applied to a skin equivalent comprising at least fibroblasts and/or keratinocytes and/or melanocytes originating from pigmentary disorders, such as age spots (actinic lentigo).

According to one of the embodiments of the method, the agent to be evaluated is a pigmentation-inhibiting agent, the depigmenting and/or anti-pigmenting activity of which it is desired to measure. The method makes it possible in particular to evaluate the effect of products intended to prevent, slow down or reduce pigmentary spots and/or other pigmentary disorders.

According to one of its embodiments, the method makes it possible to evaluate a depigmenting agent, i.e., to evaluate the ability of said agent to decrease constitutive or induced pigmentation.

According to another embodiment, the method is directed toward evaluating an anti-pigmenting agent, i.e., testing the ability of said agent to prevent and/or reduce induced pigmentation.

According to one embodiment of the invention, the product to be evaluated will be applied to a pathological model as described in the above text, for example of hyperpigmented or hypopigmented disorders such as vitiligo, melanoma, nevus, actinic lentigo, malasma, etc., using cells (melanocytes, but also keratinocytes or fibroblasts) isolated from these pathologies or which have been genetically modified (silencing, overexpression, etc.).

According to another embodiment of the method according to the invention, the agent to be evaluated is an agent for promoting pigmentation, alone or in combination with UV radiation.

According to one particular embodiment, the skin equivalents are subjected, in addition, to UV radiation, the UV radiation being applied before, concomitantly with and/or after the application of the agent to be evaluated, or applied for an equivalent period of time to the control skin equivalent.

The method according to the invention will in particular be employed for evaluating sunscreens.

The invention also makes it possible to evaluate the photoprotective power of a pigmentation-modulating agent. This will involve a comparison of the level of damage induced by UV exposure before or after pigmentation stimulation or inhibition by the agent, in particular on the formation of sunburn cells, damage to the DNA, oxidative stress, etc.

As indicated above, the skin equivalent exhibits constitutive pigmentation, and the pigmentation may, in addition, be increased by exposure to a propigmenting agent and/or to UV radiation.

In particular, after stimulation with UV radiation at doses equivalent to the daily or zenithal irradiation received by human skin of an individual under physiological conditions, the fibroblasts of the model according to the invention produce cytosoluble factors, such as cytokines or growth factors, which participate in the pigmentation and/or in the modulation thereof.

Furthermore, the number of melanocytes in the basal layer increases after UV stimulation, in particular by a factor of at least 1.5, and the morphology of said melanocytes is modified: they exhibit a marked increase in dendricity due to an increase in dendrites and also the extension thereof; the amount of melanin is also increased and through increased transfer into the epidermal layers the increase being by a factor greater than or equal to 1.5.

The increase in pigmentation is evaluated by measuring the variation in luminance of the skin, or any other methods for quantifying melanin, for instance by high performance liquid chromatography HPLC measurement, by visible spectrophotometry after dissolution of the skin with soluene or sodium hydroxide, by image analysis after staining of melanin with Fontana-Masson, or by confocal or multiphoton imaging.

The method according to the invention makes it possible to evaluate the effect, on pigmentation, of UV radiation which can act directly on the melanocytes and/or indirectly on the keratinocytes, which will in turn activate the melanocytes (action on melanogenesis, or melanocyte proliferation or adhesion).

It also makes it possible, uniquely, to evaluate the impact on pigmentation of UV radiation which can act:
on the fibroblasts, the extracellular matrix proteins, and the elements of the dermo-epidermal junction. In response, these induced factors or modifications can directly stimulate the melanocytes and/or indirectly stimulate the keratinocytes, which in turn will stimulate the melanocytes;
on the keratinocytes, which in turn will modulate the fibroblasts, the extracellular matrix proteins, and the dermo-epidermal junction elements, and consequently the pigmentation.

It also makes it possible to test products or molecules which interfere with constitutive pigmentation or pigmentation induced by sunlight (tanning): slowing down, inhibiting or stimulating, topically or systemically
depigmenting agents, anti-pigmenting agents
propigmenting agents (activators of pigmentation alone or with UV radiation).

According to one embodiment of the method of evaluation according to the invention, an additional group of measurements is also carried out with reference products known for their pigmentation-promoting activity or, conversely, their pigmentation-inhibiting activity.

In this embodiment, the pigmentation (i) of the in vitro skin equivalent to which the agent to be evaluated has been applied is also compared with that (iii) of a skin equivalent to which a pigmentation-promoting or pigmentation-inhibiting reference substance has been applied.

It will be possible, for example, to choose to retain the agents for which the pigmentation is at least greater than or equal to that observed for the reference substance, in the case of a pigmentation-promoting agent. Conversely, it will be possible to retain the agents for which the pigmentation is less than or equal to that obtained with the reference substance in the case of a depigmenting agent.

It will also be possible to compare the variation in pigmentation measured from, on the one hand, the skin equivalent to which the agent to be evaluated has been applied and the control skin equivalent (i)-(ii) and, on the other hand, the skin equivalent to which the reference substance has been applied and the control skin equivalent (iii)-(ii); the agents selected will be those for which the modulation of the pigmentation is at least equal to that measured for the reference substance.

According to one particular embodiment, the in vitro skin equivalent comprises at least keratinocytes, melanocytes and/or fibroblasts which have been genetically modified, in particular by overexpression, of cDNA, by gene quenching through site-directed mutagenesis, or with dsRNA, according to the siRNA technique or expression with shRNA.

According to another embodiment, the dermis equivalent comprises an extracellular matrix equivalent, the constituents of said extracellular matrix equivalent comprising at least collagen type I, and the constituents have undergone at least one modification compared with an extracellular matrix equivalent from healthy young skin. This may, for example, involve modification of the nature, of the amount or of the proportions of the macromolecules making up the dermis equivalent, and/or chemical modifications. The composition of the dermis equivalent, and/or the proportions, in particular, of collagen IV, laminins, entactin, fibronectin, proteoglycans, glycosaminoglycans and/or hyaluronic acid present, may thus be varied above the concentrations conventionally used and indicated in the above text. The constituents of the extracellular matrix equivalent may in particular have undergone a chemical modification selected from glycation, crosslinking and oxidation.

The method according to the invention makes it possible to provide an understanding of the pathway for regulating melanogenesis from every angle. This may be reflected by a direct activity on the melanocyte, but also by a (propigmenting or anti-pigmenting) activity mediated by the keratinocyte, the fibroblast, the entire three-dimensional context and the influence of the microenvironment.

It makes it possible to evaluate the impact, on pigmentation, of agents which can act:
- on the fibroblasts, the proteins of the extracellular matrix, and the elements of the dermo-epidermal junction. In response, these induced factors or modifications can directly stimulate the melanocytes and/or indirectly stimulate the keratinocytes, which in turn will stimulate the melanocytes;
- on the keratinocytes, which in turn will modulate the fibroblasts, the proteins of the extracellular matrix, and the elements of the dermo-epidermal junction, and consequently the pigmentation.

The method may thus be useful for:
- testing the impact on the pigmentation of cells derived from hyperpigmented or hypopigmented disorders, such as vitiligo, melanoma, nevus, actinic lentigo, melasma, etc., using cells (melanocytes but also keratinocytes or fibroblasts) which have been isolated from these pathologies or which have been genetically modified (silencing, overexpression, etc.);
- studying the influence of keratinocyte or fibroblast disruptions (pathological keratinocytes or fibroblasts) on the pigmentation;
- for studying the influence of disruptions of the extracellular matrix on the pigmentation (glycation, bridging (crosslinking)), oxidation of the macromolecules of the extracellular matrix, or modifications of the nature, of the amount and of the proportion of the macromolecules.

The invention also features a kit for producing a reconstructed skin comprising a dermal support, melanocytes and keratinocytes, and also the media described above.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Preparation of the Skin Equivalents

Preparation of the Lattices (D-4):
The dermis equivalents are prepared with bovine collagen I and human fibroblasts derived from dermis.

The dermis equivalents are prepared with bovine collagen I and human fibroblasts derived from dermis according to the techniques described by Asselineau et al., 1985 (*Exp Cell Res.*, vol. 159, 536-539) and Bernerd and Asselineau 1997 (*Dev Biol.*, vol. 183, 123-138). The Petri dish was precoated with MEM containing 10% of serum.

Before pouring the collagen preparation containing the cells, a solution of laminin (3%/final volume), collagen IV (1.5%/final volume) and entactin (0.35%/final volume) is added to the mixture, which is stirred vigorously. This suspension is placed in an incubator (37° C.-5% $CO_2$) so as to allow the lattice to contract.

Seeding of the Keratinocytes and the Melanocytes (D0):
The keratinocytes and melanocytes are seeded on the dermis equivalent after contraction of the lattices.

For this, the cells are amplified 7 days before seeding, in their respective growth medium:

The melanocytes are amplified in a culture medium for melanocytes, M2 medium (Promocell) in the absence of any phorbol ester.

The keratinocytes are amplified according to the technique of Rheinwald and Green, *Cell*, vol. 6, 331-344, 1975, by culture on a feeder support constituted of 3T3 fibroblasts.

For seeding the keratinocytes and the melanocytes on the dermis equivalent, the lattice is first attached to the bottom of a dish using a collagen-based preparation (for 2 lattices, 0.46 ml of 1.76×MEM+0:09 ml of FCS+0.05 ml of 0.1N NaOH+0.1 ml of MEM Hepes 10% FCS+0.3 ml of dialyzed collagen).

The melanocytes and the keratinocytes are trypsinized and the cell suspensions are adjusted to a concentration of 200,000 cells/ml, each with medium constituted of MEM 10% FCS+2 mM L-glutamine+1 mM sodium pyrUV-Ate+ 1× nonessential amino acids+0.2% penicillin/streptomycin+ 0.1% antimycotic antibiotic+10 ng/ml EGF, $10^{-10}$ M cholera toxin+0.4 µg/ml hydrocortisone+0.625 µl/ml of supplement mix (Promocell)=PRP medium.

A mixed suspension of melanocytes and keratinocytes is prepared with 0.25 ml of the keratinocyte suspension and 0.25 ml of melanocyte suspension. The final suspension thus containing 50,000 keratinocytes and 50,000 melanocytes is deposited inside a ring (14 mm in diameter) placed on the attached lattice. 6 ml of PRP medium are added around the ring.

The dishes are placed in an incubator at 37° C.-5% $CO_2$. After 2 hours, the rings are removed. The same culture medium is refreshed 2 days later.

4 days after seeding, the EGF (10 ng/ml) of the PRP medium is replaced with KGF (10 ng/ml).

Immersion-culture of the Pigmented Reconstructed Skins (D7):

After 7 days of immersion-culture, the skins are immersed on a screen (air-liquid interface). The medium is changed every 2 days.

After 7 days of immersion, the skins exhibiting a morphology very close to normal human skin are ready to be removed and analyzed or can be maintained in culture for a longer period of time for various experiments, with the medium being changed every 2 days.

EXAMPLE 2

Human Pigmented Reconstructed Skin Containing the 3 Cell Types: Melanocytes, Keratinocytes and Fibroblasts (FIG. 1)

After 7 days of immersion, the skin exhibits a histology and a three-dimensional architecture close to that of human skin.

It has a stratified and differentiated epidermis made up of the various cell layers (basal, prickle-cell, granular) and a horny layer.

Figure 1:
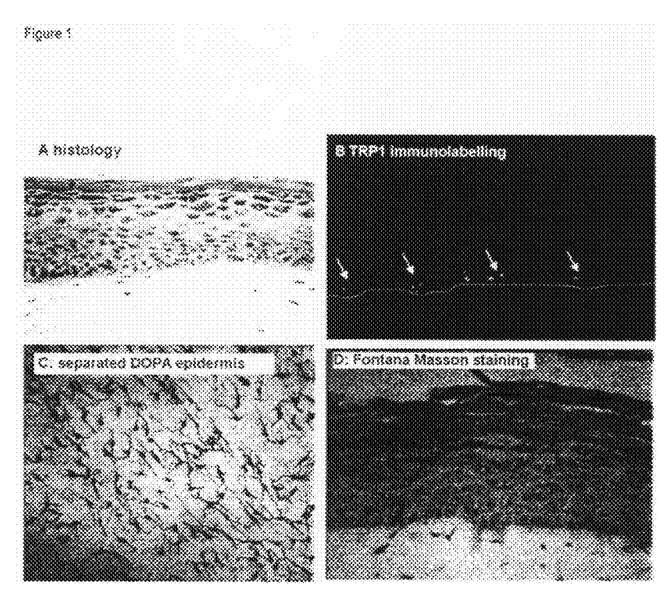
FIG. 1 illustrates human pigmented reconstructed skin.

The dermis comprises live fibroblasts embedded in the collagen matrix (FIG. 1A).

The melanocytes are integrated into the epidermis and show a morphology and a density similar to those of normal skin (FIG. 1C, DOPA reaction on separated epidermis). They are clearly localized in the basal layer (FIG. 1B, TRP1 immunolabeling, the dashed white line indicating the dermo-epidermal junction), and produce melanosomes and melanin which are transferred into the neighboring keratinocytes (FIG. 1D, staining of melanin with Fontana-Masson).

EXAMPLE 3

Figure 2:
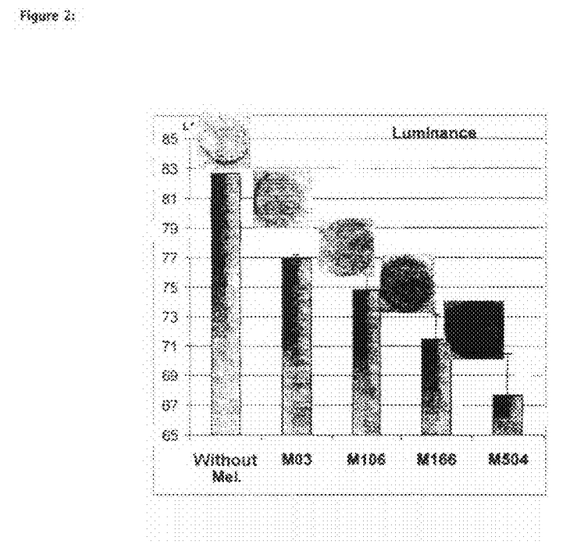
FIG. 2 illustrates human pigmented reconstructed skin with constitutive pigmentation linked to the type of melanocyte.

Human Pigmented Reconstructed Skin with Constitutive Pigmentation Linked to the Melanocyte Type (FIG. 2)

The model is capable of integrating various melanocyte strains, from the least pigmented to the most pigmented (sound model) and the phenotype of the reconstructed skin, which is more or less pigmented, corresponds to the melanocyte type used (physiology maintained): in fact, the more pigmented the melanocyte strain (from M03 to M504), the stronger the macroscopic color of the skin and the greater the amount of melanin visible on the section. This macroscopic pigmentation is reflected by a decrease in luminance (FIG. 2, Luminance).

EXAMPLE 4

Figure 3:
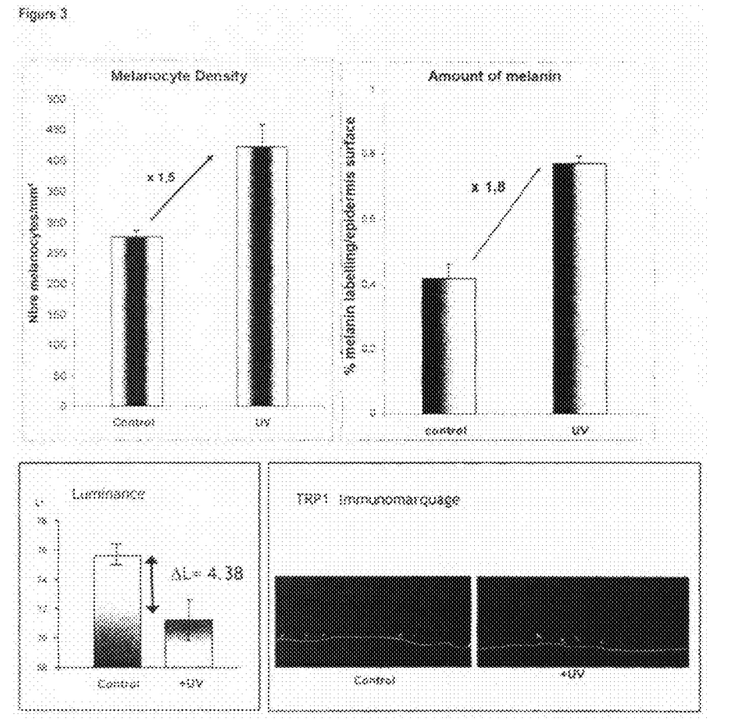
FIG. 3 illustrates induction of pigmentation with UV radiation, in the pigmented reconstructed skin.

Induction of Pigmentation by UV Radiation, in the Pigmented Reconstructed Skin (FIG. 3):

Starting from 7 days of immersion, the reconstructed skins are subjected to solar UV radiation so as to induce pigmentation. A solar simulator is used: it delivers UV-B radiation and UV-A radiation with a spectrum comparable to that of the sun (UV-B/UV-A ratio of 14). The skins are exposed to the UV-B radiation 3 times, once every 2 days. The skins are removed 48 h after the final exposure. Control conditions are carried out in the absence of exposure to the solar simulator.

In the skins subjected to UV radiation, the melanocytes are still present and clearly localized in the basal layer (FIG. 3, TRP1 immunolabeling. The dashed white line indicates the dermo-epidermal junction). They are activated by the UV radiation: there are more of them (FIG. 3, melanocyte density graph), and they are more dendritic and more Dopa-reaction-reactive than in the unexposed skins. An increase in the amount of melanin is measured (×1.8) after Fontana-Masson staining in the light-exposed skins compared with the control skins (FIG. 3, amount of melanin). This stimulation of pigmentation by UV radiation is quantified by measuring the luminance (L*): the decrease in luminance (ΔL=4.38) shows that the UV-exposed skins are darker than the unexposed skins (FIG. 3, Luminance).

EXAMPLE 5

Figure 4:
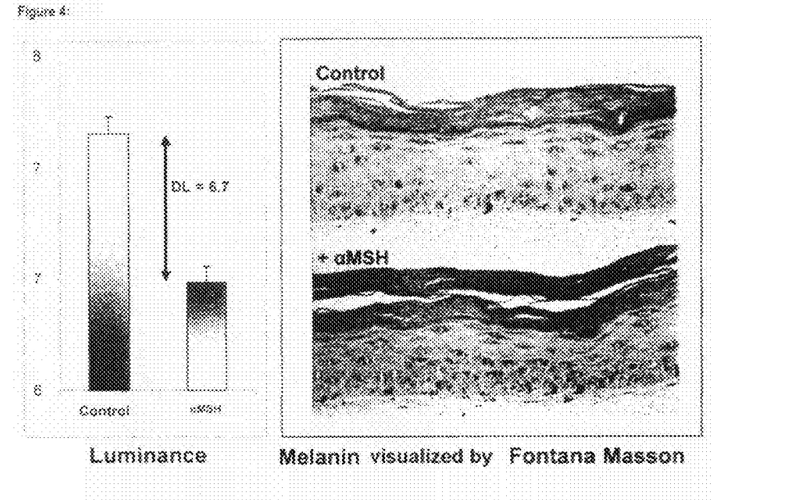
FIG. 4 illustrates induction of pigmentation with alpha-MSH, in the pigmented reconstructed skin according to the invention.

Induction of Pigmentation in the Pigmented Reconstructed Skin with a Propigmenting Agent (FIG. 4)

In the presence of a known propigmenting agent, αMSH, placed in the medium starting from the immersion phase and at a concentration of 50 nM, the skins taken 18 days later are macroscopically more pigmented. The luminance measurement confirms this browning since it decreases by 6.7 points from the untreated skins and those treated with αMSH (FIG. 4, Luminance).

The melanocytes are more dendritic and produce much more melanin visible by Fontana-Masson labeling in the presence of αMSH (FIG. 4, Fontana-Masson staining).

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An in vitro skin model comprised on a support that is selected or treated such that collagen matrix does not adhere to the support, the model consisting essentially of cultured melanocytes, cultured keratinocytes, cultured fibroblasts, and a free collagen matrix consisting essentially of one or more collagens and optionally one or more extracellular matrix constituents selected among laminins, entactin, fibronectin, proteoglycans, glycosaminoglycans and hyaluronic acid, the skin model forming at least one epidermis model and at least one dermis model having the free collagen matrix wherein cultured keratinocytes form at least one basal layer and at least one superficial layer of the epidermis model, wherein cultured melanocytes constitutively produce melanin, wherein all of the melanocytes are situated in the basal layer of the epidermis model, wherein in the dermis model, the percentage of fibroblasts oriented longitudinally relative to the surface of the dermis model is less than 50%, and wherein the free collagen matrix is contractile in all directions, is not taut, and does not adhere to the support.

2. The in vitro skin model as defined by claim 1, wherein the free collagen matrix is a matrix of collagen type I in which the fibroblasts are distributed.

3. The in vitro skin model as defined by claim 1, wherein the melanocytes are melanocytes originating from human skin.

4. The skin model as defined by claim 1, wherein the pigmentation thereof is increased by exposure to a propigmenting agent and/or to UV radiation.

5. An in vitro skin model consisting essentially of cultured melanocytes, cultured keratinocytes, cultured fibroblasts, and a free collagen matrix consisting essentially of one or more collagens and optionally one or more extracellular matrix constituents selected among laminins, entactin, fibronectin, proteoglycans, glycosaminoglycans and hyaluronic acid, the skin model forming at least one epidermis model and at least one dermis model having the free collagen matrix, the model being obtained by a method of preparation on a support selected or treated such that collagen matrix does not adhere to the support, the method comprising:
    a) contacting fibroblasts and a solution of collagen, then incubating same for a sufficient period of time to provide a contracted collagen matrix in which the fibroblasts are distributed, constituting a dermis model,
    b) seeding the dermis model with a mixture of keratinocytes and melanocytes on the dermis equivalent obtained in a), and c) immersing the culture of keratinocytes and of melanocytes on the dermis model obtained in b) in a liquid medium, and continuing the culture at the air-liquid interface until a pluristratified epidermis equivalent containing melanocytes, on a dermis model containing fibroblasts in a collagen matrix is obtained, wherein the in vitro skin model comprises at least one epidermis model which contains keratinocytes forming at least one basal layer and at least one superficial layer, and at least one dermis model, wherein the dermis model comprises a free collagen matrix, said skin model comprising melanocytes constitutively producing melanin and live fibroblasts, all of the melanocytes being situated in the basal layer of said epidermis model, and the percentage of fibroblasts oriented longitudinally relative to the surface of the dermis model is less than 50%, and wherein the free collagen matrix is contractile in all directions, is not taut, and does not adhere to a support.

6. The in vitro skin model as defined by claim 5, wherein the melanocytes are human melanocytes obtained from adult skin and amplified beforehand.

7. The in vitro skin model as defined by claim 5, wherein the keratinocytes and the fibroblasts are obtained from adult human skin.

8. The in vitro skin model as defined by claim 5, wherein step a) is carried out in the presence of collagen IV, laminin, and/or entactin.

9. The in vitro skin model as defined by claim 5, wherein the method of preparation does not employ a mutagenic substance, and the cells do not exhibit any modifications of tumor type.

10. The in vitro skin model as defined by claim 1, wherein the skin equivalent is made without employing a mutagenic substance, and the cells do not exhibit any modifications of tumor type.

11. An in vitro skin model according to claim 1, wherein said support does not allow adhesion of said matrix.

12. An in vitro skin model according to claim 5, wherein said support does not allow adhesion of said matrix.

13. An in vitro skin model according to claim 1, wherein said support is coated with bovine serum albumin or serum.

14. An in vitro skin model according to claim 5, wherein said support is coated with bovine serum albumin or serum.

* * * * *